(12) United States Patent
Pellechia

(10) Patent No.: US 7,919,581 B2
(45) Date of Patent: Apr. 5, 2011

(54) BI-DENTATE COMPOUNDS AS KINASE INHIBITORS

(75) Inventor: Maurizio Pellechia, San Diego, CA (US)

(73) Assignee: Burnham Institute for Medical Research, San Diego, CA (US)

( * ) Notice: Subject to any disclaimer, the term of this patent is extended or adjusted under 35 U.S.C. 154(b) by 142 days.

(21) Appl. No.: 12/184,208

(22) Filed: Jul. 31, 2008

(65) Prior Publication Data

US 2009/0054348 A1 Feb. 26, 2009

Related U.S. Application Data

(60) Provisional application No. 60/962,778, filed on Jul. 31, 2007.

(51) Int. Cl.
*A61K 38/04* (2006.01)
*A61K 38/06* (2006.01)

(52) U.S. Cl. ......... 530/328; 530/329; 530/330; 530/331

(58) Field of Classification Search ........................ None
See application file for complete search history.

(56) References Cited

U.S. PATENT DOCUMENTS

| 6,559,279 B1 * | 5/2003 | Manoharan et al. ........ 530/322 |
| 6,753,313 B1 | 6/2004 | Dasseux et al. ............... 514/12 |
| 2005/0019824 A1 | 1/2005 | Alderson et al. ................. 435/6 |
| 2007/0083334 A1 | 4/2007 | Mintz et al. ..................... 702/19 |
| 2007/0111926 A1 | 5/2007 | Zundel et al. ..................... 514/3 |
| 2007/0161648 A1 | 7/2007 | Hughes et al. ........... 514/254.06 |

FOREIGN PATENT DOCUMENTS

WO 2004/100996 * 5/2004

OTHER PUBLICATIONS

Salh. c-Jun N-terminal kinases as potential therapeutic targets. Review. Expert Opin. Ther. Targets. 2007. vol. 11, No. 10, pp. 1339-1353.*
Barr et al. Identification of the Critical Features of a Small Peptide Inhibitor of JNK Activity. The Journal of Biological Chemistry. 2002, vol. 277, No. 13, pp. 10987-10997.*

* cited by examiner

*Primary Examiner* — Marcela M Cordero Garcia
(74) *Attorney, Agent, or Firm* — DLA Piper LLP (US)

(57) ABSTRACT

The present invention provides compound having the general structure A or pharmaceutically acceptable salts thereof:

Het-L-P (A)

wherein Het is an aromatic moiety comprising a heterocyclic structure mimicking ATP, P is a docking site derived peptide or a docking site peptide mimetic, and L is a linking moiety, wherein L links the ATP mimetic to the docking site peptide moiety. The compounds having the general structure A can serve as inhibitors of kinases, such as the kinases JNK, Erk and p38.

18 Claims, 4 Drawing Sheets

Log [Ac-RPTTLNLGG-OH] μM

Log [Compound I] nM

Log [Product 8] μM

Log [Compound I] μM

```
                        SEQUENCE LISTING

<160> NUMBER OF SEQ ID NOS: 16

<210> SEQ ID NO 1
<211> LENGTH: 9
<212> TYPE: PRT
<213> ORGANISM: Artificial sequence
<220> FEATURE:
<223> OTHER INFORMATION: Synthetic construct

<400> SEQUENCE: 1

Arg Pro Thr Thr Leu Asn Leu Gly Gly
1               5

<210> SEQ ID NO 2
<211> LENGTH: 8
<212> TYPE: PRT
<213> ORGANISM: Artificial sequence
<220> FEATURE:
<223> OTHER INFORMATION: Synthetic construct

<400> SEQUENCE: 2

Pro Thr Thr Leu Asn Leu Gly Gly
1               5

<210> SEQ ID NO 3
<211> LENGTH: 5
<212> TYPE: PRT
<213> ORGANISM: Artificial sequence
<220> FEATURE:
<223> OTHER INFORMATION: Synthetic construct

<400> SEQUENCE: 3

Leu Asn Leu Gly Gly
1               5

<210> SEQ ID NO 4
<211> LENGTH: 7
<212> TYPE: PRT
<213> ORGANISM: Artificial sequence
<220> FEATURE:
<223> OTHER INFORMATION: Synthetic construct

<400> SEQUENCE: 4

Arg Pro Thr Thr Leu Asn Leu
1               5

<210> SEQ ID NO 5
<211> LENGTH: 21
<212> TYPE: PRT
<213> ORGANISM: Artificial sequence
<220> FEATURE:
<223> OTHER INFORMATION: Synthetic construct

<400> SEQUENCE: 5

Gly Arg Lys Lys Arg Arg Gln Arg Arg Gly Gly Arg Pro Thr Thr
1               5                   10                  15
```

```
Leu Asn Leu Gly Gly
            20

<210> SEQ ID NO 6
<211> LENGTH: 21
<212> TYPE: PRT
<213> ORGANISM: Artificial sequence
<220> FEATURE:
<223> OTHER INFORMATION: Synthetic construct

<400> SEQUENCE: 6

Gly Gly Leu Asn Leu Thr Thr Pro Arg Gly Arg Arg Gln Arg
1               5                   10                  15

Arg Lys Lys Arg Gly
            20

<210> SEQ ID NO 7
<211> LENGTH: 10
<212> TYPE: PRT
<213> ORGANISM: Artificial sequence
<220> FEATURE:
<223> OTHER INFORMATION: Synthetic construct

<400> SEQUENCE: 7

Gly Arg Pro Thr Thr Leu Asn Leu Gly Gly
1               5                   10

<210> SEQ ID NO 8
<211> LENGTH: 21
<212> TYPE: PRT
<213> ORGANISM: Artificial sequence
<220> FEATURE:
<223> OTHER INFORMATION: Synthetic construct
<220> FEATURE:
<221> NAME/KEY: misc_feature
<222> LOCATION: (1)..(8)
<223> OTHER INFORMATION: Xaa can be any naturally occurring amino acid
<220> FEATURE:
<221> NAME/KEY: misc_feature
<222> LOCATION: (14)..(21)
<223> OTHER INFORMATION: Xaa can be any naturally occurring amino acid

<400> SEQUENCE: 8

Xaa Xaa Xaa Xaa Xaa Xaa Xaa Xaa Leu Asn Leu Gly Gly Xaa Xaa Xaa
1               5                   10                  15

Xaa Xaa Xaa Xaa Xaa
            20

<210> SEQ ID NO 9
<211> LENGTH: 19
<212> TYPE: PRT
<213> ORGANISM: Artificial sequence
<220> FEATURE:
<223> OTHER INFORMATION: Synthetic construct
<220> FEATURE:
<221> NAME/KEY: misc_feature
<222> LOCATION: (1)..(8)
<223> OTHER INFORMATION: Xaa can be any naturally occurring amino acid
<220> FEATURE:
<221> NAME/KEY: misc_feature
<222> LOCATION: (12)..(19)
<223> OTHER INFORMATION: Xaa can be any naturally occurring amino acid

<400> SEQUENCE: 9

Xaa Xaa Xaa Xaa Xaa Xaa Xaa Xaa Leu Asn Leu Xaa Xaa Xaa Xaa Xaa
1               5                   10                  15

Xaa Xaa Xaa
```

```
<210> SEQ ID NO 10
<211> LENGTH: 6
<212> TYPE: PRT
<213> ORGANISM: Artificial sequence
<220> FEATURE:
<223> OTHER INFORMATION: Synthetic construct

<400> SEQUENCE: 10

Pro Thr Thr Leu Asn Leu
1               5

<210> SEQ ID NO 11
<211> LENGTH: 9
<212> TYPE: PRT
<213> ORGANISM: Artificial sequence
<220> FEATURE:
<223> OTHER INFORMATION: Synthetic construct

<400> SEQUENCE: 11

Gly Gly Leu Asn Leu Thr Thr Pro Arg
1               5

<210> SEQ ID NO 12
<211> LENGTH: 8
<212> TYPE: PRT
<213> ORGANISM: Artificial sequence
<220> FEATURE:
<223> OTHER INFORMATION: Synthetic construct

<400> SEQUENCE: 12

Gly Gly Leu Asn Leu Thr Thr Pro
1               5

<210> SEQ ID NO 13
<211> LENGTH: 5
<212> TYPE: PRT
<213> ORGANISM: Artificial sequence
<220> FEATURE:
<223> OTHER INFORMATION: Synthetic construct

<400> SEQUENCE: 13

Gly Gly Leu Asn Leu
1               5

<210> SEQ ID NO 14
<211> LENGTH: 7
<212> TYPE: PRT
<213> ORGANISM: Artificial sequence
<220> FEATURE:
<223> OTHER INFORMATION: Synthetic construct

<400> SEQUENCE: 14

Leu Asn Leu Thr Thr Pro Arg
1               5

<210> SEQ ID NO 15
<211> LENGTH: 6
<212> TYPE: PRT
<213> ORGANISM: Artificial sequence
<220> FEATURE:
<223> OTHER INFORMATION: Synthetic construct

<400> SEQUENCE: 15

Leu Asn Leu Thr Thr Pro
1               5

<210> SEQ ID NO 16
<211> LENGTH: 11
```

```
<212> TYPE: PRT
<213> ORGANISM: Artificial sequence
<220> FEATURE:
<223> OTHER INFORMATION: Synthetic construct

<400> SEQUENCE: 16

Arg Pro Lys Arg Pro Thr Thr Leu Asn Leu Phe
1               5                   10
```

BI-DENTATE COMPOUNDS AS KINASE INHIBITORS

CROSS-REFERENCE TO RELATED APPLICATIONS

This application claims priority under 35 U.S.C. §119(e) to U.S. Patent Application Ser. No. 60/962,778 filed Jul. 31, 2008, which is herein incorporated by reference in its entirety.

BACKGROUND

1. Field of the Invention

The present invention relates generally to compounds useful for the inhibition of kinases, and more specifically, to bi-dentate compounds that are useful as kinase inhibitors.

2. Background Information

Protein kinases are families of enzymes that catalyze the phosphorylation of specific residues in proteins, and may be broadly classified into tyrosine or serine/threonine kinases based on the amino acids phosphorylated. This covalent post-translational modification is a pivotal component of normal cellular communication and maintenance of homeostasis.

There is a body of evidence linking kinase misregulation, dysregulation and mutation to a variety of disorders including cancer, diabetes, ocular diseases and other indications. Inappropriate kinase activity triggers a variety of biological cellular responses relating to cell growth, cell differentiation, survival, apoptosis, mitogenesis, cell cycle control, and cell mobility implicated in the above-mentioned and other diseases.

Accordingly, inhibiting kinases, such as C-Jun N-terminal kinase (JNK), is one method of treating various diseases, disorders and pathologies associated with kinases. Previously, some compounds that can be useful as inhibitors of certain kinases, and which target the ATP binding site of the protein, have been identified and synthesized.

While some JNK-interacting peptides (JIP) and JIP mimics capable of doing so have been described previously, no compounds have been reported that are capable of targeting and inhibiting JNK kinase binding to the docking site (JIP site) for the substrate or scaffolding proteins and the ATP binding site at the same time.

SUMMARY

Currently, there is a need for identifying potent and selective agents for the treatment of various diseases, disorders and pathologies, such as tumors, as well as for the pharmaceutical compositions including such agents. Such agents can be based on inhibition of certain kinases, such as JNK kinase.

In addition a few JNK-interacting peptides (JIP) and JIP mimics capable of inhibiting JNK have been also described. These JIP mimics tend to be specific but with modest affinities. In the present invention, compounds are described for the first time that are capable of targeting and inhibiting JNK kinase by binding to both the docking site (JIP site) for the substrate or scaffolding proteins and the ATP site. These compounds are thus both potent and specific.

According to embodiments of the present invention, there are provided compounds having the general structure A or pharmaceutically acceptable salts thereof:

$$\text{Het-L-P} \qquad (A)$$

wherein Het is an aromatic moiety comprising a heterocyclic structure, P is a peptide moiety comprising a peptide or a polypeptide, and L is a linking moiety, wherein L links the aromatic moiety to the peptide moiety.

In some embodiments of the present invention, in the compounds having the general structure A shown above, the aromatic moiety Het comprises a heterocyclic structure that includes a derivative of indazole. For example, the aromatic moiety Het comprises the following, indazole-based, moiety:

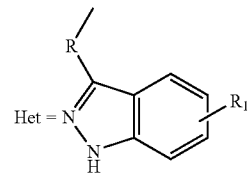

wherein R is an aromatic substituent, and $R_1$ is hydrogen or a substitutent selected from a group consisting of a straight-chained alkyl, a branched alkyl, and a halogen, and wherein the moiety Het is connected to the linking moiety via the aromatic substitutent R.

According to some embodiments of the present invention, compounds are provided having the formulae wherein the compounds I-VII comprise SEQ ID NO:s 1 to 7 and compound VIII comprises SEQ ID NO:1, accordingly:

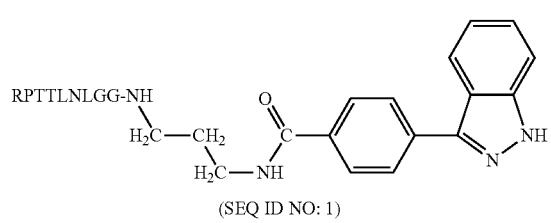

I (SEQ ID NO: 1)

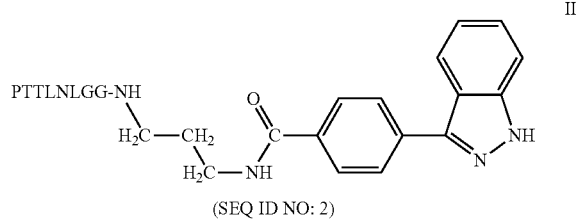

II (SEQ ID NO: 2)

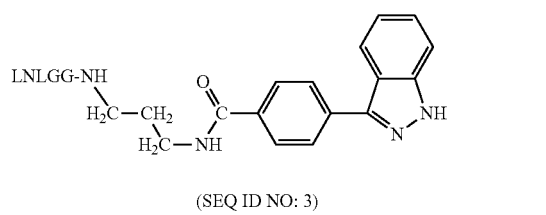

III (SEQ ID NO: 3)

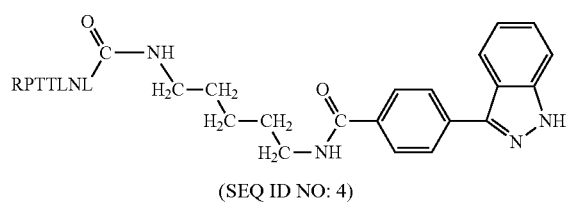

IV (SEQ ID NO: 4)

-continued

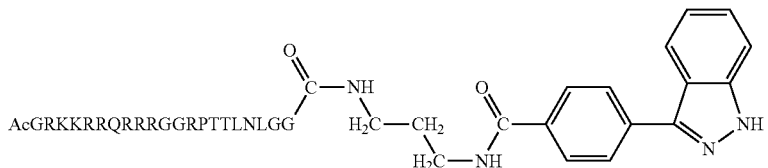

(SEQ ID NO: 5)

V

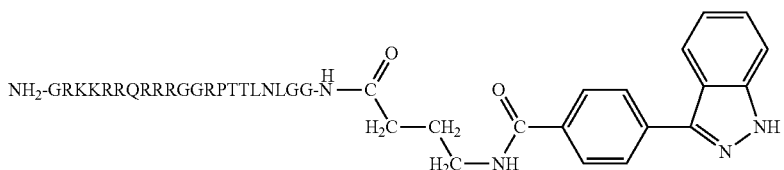

(SEQ ID NO: 6 (D amino acids))

VI

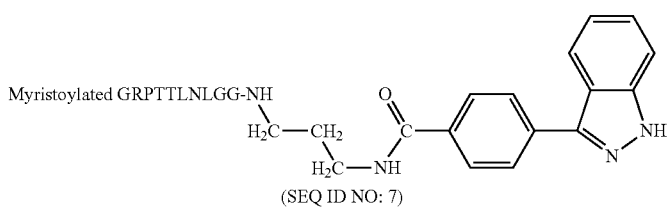

(SEQ ID NO: 7)

VII

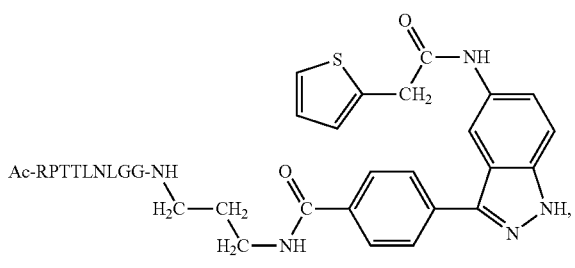

(SEQ ID NO: 1)

VIII wherein SEQ ID NO:1 is RPTTLNLGG; SEQ ID NO:2 is PTTLNLGG; SEQ ID NO:3 is LNLGG; SEQ ID NO:4 is RPTTLNL; SEQ ID NO:5 is GRKKRRQRRRGGRPTTLNLGG; SEQ ID NO:6 is GRKKRRQRRRGGRPTTLNLGG (D amino acids); and SEQ ID NO:7 is GRPTTLNLGG.

According to other embodiments of the present invention, pharmaceutical compositions are provided for the treatment of various disorders, diseases, and pathologies, such as cancer, diabetes, and neurological disorders, the compositions comprising a compound having the general structure A, and a pharmaceutically acceptable carrier.

According to other embodiments of the present invention, methods for the treatment of various disorders, diseases, and pathologies, such as cancer, diabetes and neurological disorders, are provided, the methods comprising administering to a subject in need thereof a pharmacologically effective dose of a pharmaceutical composition comprising a compound having the general structure A.

DETAILED DESCRIPTION

Figure 1A:
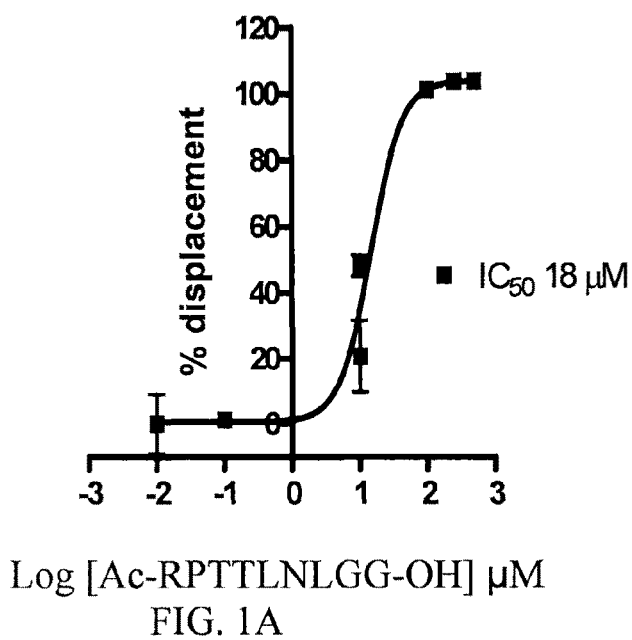
FIG. 1A illustrates kinase inhibition by the peptide Ac-RPTTLNLGG-OH (SEQ ID NO:1), which illustration is provided for the purposes of comparison.

The term "alkyl" refers to either substituted or unsubstituted $C_1$-$C_{10}$ straight chain saturated aliphatic hydrocarbon groups, substituted and unsubstituted $C_2$-$C_{10}$ straight chain unsaturated aliphatic hydrocarbon groups, substituted and unsubstituted $C_4$-$C_{10}$ branched saturated aliphatic hydrocarbon groups, substituted and unsubstituted $C_4$-$C_{10}$ branched unsaturated aliphatic hydrocarbon groups, substituted and unsubstituted $C_3$-$C_8$ cyclic saturated aliphatic hydrocarbon groups, substituted and unsubstituted $C_5$-$C_8$ cyclic unsaturated aliphatic hydrocarbon groups having the specified number of carbon atoms. For example, the definition of "alkyl" shall include but is not limited to: methyl, ethyl, propyl, butyl, pentyl, hexyl, heptyl, octyl, nonyl, decyl, undecyl, ethenyl, propenyl, butenyl, penentyl, hexenyl, heptenyl, octenyl, nonenyl, decenyl, undecenyl, isopropyl, isobutyl, tert-butyl, sec-butyl, isopentyl, neopentyl, cyclopropyl, cyclobutyl, cyclopentyl, cyclohexyl, cycloheptyl, cyclooctyl, cyclopentenyl, cyclohexenyl, cycloheptenyl, cyclooctenyl, methylcyclopropyl, ethylcyclohexenyl, butenylcyclopentyl, adamantyl, norbornyl and the like.

Alkyl substituents are independently selected from a group consisting of halogen, —OH, —SH, —NH$_2$, —CN, —NO$_2$, =O, =CH$_2$, trihalomethyl, carbamoyl, arylC$_{0-10}$alkyl, heteroarylC$_{0-10}$alkyl, C$_{1-10}$alkyloxy, arylC$_{0-10}$alkyloxy, C$_{1-10}$alkylthio, arylC$_{0-10}$alkylthio, C$_{1-10}$alkylamino, arylC$_{0-10}$alkylamino, N-aryl-N—C$_{0-10}$alkylamino, C$_{1-10}$alkylcarbonyl, arylC$_{0-10}$alkylcarbonyl, C$_{1-10}$alkylcarboxy, arylC$_{0-10}$alkylcarboxy, C$_{1-10}$alkylcarbonylamino, arylC$_{0-10}$alkylcarbonylamino, tetrahydrofuryl, morpholinyl, piperazinyl, hydroxypyronyl, —C$_{0-10}$alkylCOOR$_a$ and —C$_{0-10}$alkylCONR$_b$R$_c$, wherein R$_a$, R$_b$ and R$_c$ are independently selected from hydrogen, alkyl, aryl, or R$_b$ and R$_c$ are taken together with the nitrogen to which they are attached forming a saturated cyclic or unsaturated cyclic system containing 3 to 8 carbon atoms, with at least one substituent.

The term "aryl" refers to an unsubstituted, mono-, di- or trisubstituted monocyclic, polycyclic, biaryl aromatic groups covalently attached at any ring position capable of forming a stable covalent bond, certain preferred points of attachment being apparent to those skilled in the art (e.g., 3-phenyl, 4-naphtyl and the like). The aryl substituents are independently selected from a group consisting of halogen, —OH, —SH, CN, —NO$_2$, trihalomethyl, hydroxypyronyl, C$_{1-10}$alkyl, arylC$_{0-10}$alkyl, C$_{0-10}$alkyloxyC$_{0-10}$alkyl, arylC$_{0-10}$alkyloxyC$_{0-10}$alkyl, C$_{0-10}$alkylthioC$_{0-10}$alkyl, arylC$_{0-10}$alkylthioC$_{0-10}$alkyl, C$_{0-10}$alkylaminoC$_{0-10}$alkyl, arylC$_{0-10}$alkylaminoC$_{0-10}$alkyl, N-aryl-N—C$_{0-10}$alkylaminoC$_{0-10}$alkyl, C$_{1-10}$alkylcarbonylC$_{0-10}$alkyl, arylC$_{0-10}$alkylcarbonylC$_{0-10}$alkyl, C$_{1-10}$alkylcarboxyC$_{0-10}$alkyl, arylC$_{0-10}$alkylcarboxyC$_{0-10}$alkyl, C$_{1-10}$alkylcarbonylaminoC$_{0-10}$alkyl, arylC$_{0-10}$alkylcarbonylaminoC$_{0-10}$alkyl, —C$_{0-10}$alkylCOOR$_a$, and —C$_{0-10}$alkylCONR$_b$R$_c$, wherein R$_a$, R$_b$ and R$_c$ are independently selected from hydrogen, alkyl, aryl or R$_b$ and R$_c$ are taken together with the nitrogen to which they are attached forming a saturated cyclic or unsaturated cyclic system containing 3 to 8 carbon atoms with at least one substituent.

The definition of "aryl" includes, but is not limited to, such specific groups as phenyl, biphenyl, naphthyl, dihydronaphthyl, tetrahydronaphthyl, indenyl, indanyl, azulenyl, anthryl, phenanthryl, fluorenyl, pyrenyl and the like.

The terms "heteroaryl", "heterocycle" or "heterocyclic" refer to a monovalent unsaturated group having a single ring or multiple condensed (also known as "fused") rings, from 1 to 8 carbon atoms and from 1 to 4 hetero atoms selected from nitrogen, sulfur or oxygen within the ring. The heteroaryl groups in this invention can be optionally substituted with 1 to 3 substituents selected from a group consisting of: halogen, —OH, —SH, —N, —NO$_2$, trihalomethyl, hydroxypyronyl, C$_{1-10}$alkyl, arylC$_{0-10}$alkyl, C$_{0-10}$alkyloxyC$_{0-10}$alkyl, arylC$_{0-10}$alkyloxyC$_{0-10}$alkyl, C$_{0-10}$alkylthioC$_{0-10}$alkyl, arylC$_{0-10}$alkylthioC$_{0-10}$alkyl, C$_{0-10}$alkylaminoC$_{0-10}$alkyl, arylC$_{0-10}$alkylaminoC$_{0-10}$alkyl, N-aryl-N—C$_{0-10}$alkylaminoC$_{0-10}$alkyl, C$_{1-10}$alkylcarbonylC$_{0-10}$alkyl, arylC$_{0-10}$alkylcarbonylC$_{0-10}$alkyl, C$_{1-10}$alkylcarboxyC$_{0-10}$alkyl, arylC$_{0-10}$alkylcarboxyC$_{0-10}$alkyl, C$_{1-10}$alkylcarbonylaminoC$_{0-10}$alkyl, arylC$_{0-10}$alkylcarbonylaminoC$_{0-10}$alkyl, —C$_{0-10}$alkylCOOR$_a$, and —C$_{0-10}$alkylCONR$_b$R$_c$ wherein R$_a$, R$_b$ and R$_c$ are independently selected from hydrogen, alkyl, aryl, or R$_b$ and R$_c$ are taken together with the nitrogen to which they are attached forming a saturated cyclic or unsaturated cyclic system containing 3 to 8 carbon atoms with at least one substituent.

The definition of "heteroaryl" includes, but is not limited to, such specific groups as thienyl, benzothienyl, isobenzothienyl, 2,3-dihydrobenzothienyl, furyl, pyranyl, benzofuranyl, isobenzofuranyl, 2,3-dihydrobenzofuranyl, pyrrolyl, pyrrolyl-2,5-dione, 3-pyrrolinyl, indolyl, isoindolyl, 3H-indolyl, indolinyl, indolizinyl, indazolyl, phthalimidyl (or isoindolyl-1,3-dione), imidazolyl, 2H-imidazolinyl, benzimidazolyl, pyridyl, pyrazinyl, pyradazinyl, pyrimidinyl, triazinyl, quinolyl, isoquinolyl, 4H-quinolizinyl, cinnolinyl, phthalazinyl, quinazolinyl, quinoxalinyl, 1,8-naphthyridinyl, pteridinyl, carbazolyl, acridinyl, phenazinyl, phenothiazinyl, phenoxazinyl, chromanyl, benzodioxolyl, piperonyl, purinyl, pyrazolyl, triazolyl, tetrazolyl, thiazolyl, isothiazolyl, benzthiazolyl, oxazolyl, isoxazolyl, benzoxazolyl, oxadiazolyl, thiadiazolyl, pyrrolidinyl-2,5-dione, imidazolidinyl-2,4-dione, 2-thioxo-imidazolidinyl-4-one, imidazolidinyl-2,4-dithione, thiazolidinyl-2,4-dione, 4-thioxo-thiazolidinyl-2-one, piperazinyl-2,5-dione, tetrahydro-pyridazinyl-3,6-dione, 1,2-dihydro-[1,2,4,5]tetrazinyl-3,6-dione, [1,2,4,5]tetrazinanyl-3,6-dione, dihydro-pyrimidinyl-2,4-dione, pyrimidinyl-2,4,6-trione and the like.

The term "indazole" refers to a bicyclic heteroaryl having the formula

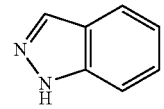

The terms "halogen", "halide" or "halo" refer to fluorine, chlorine, bromine, and iodine.

The terms "peptide" and "polypeptide" refer to molecular chains formed by a plurality of amino acids which are formed by condensation of the amino group of one acid with the carboxyl group of another.

The term a "derivative" in connection with a peptide moiety refers to a form of the peptide in which one or more reaction groups of the compound have been derivatized with a substituent group.

The term "an analog" in connection with a peptide moiety refers to a compound which retains chemical structures necessary for functional activity, yet which also contains certain chemical structures which differ from the parent peptide.

The term "kinase" refers to any enzyme that catalyzes the addition of phosphate groups to a protein residue; for example, serine and threonine kinases catalyze the addition of phosphate groups to serine and threonine residues.

The term "JNK kinase" refers to JNK, also known as C-Jun N-terminal kinase, which is a kinase that binds and phosphosphorylates c-Jun on Ser63 and Ser73 within its transcriptional activation domain, and is amitogen-activated protein kinase which is responsive to stress stimuli, such as cytokines ultraviolet irradiation, heat shock, and osmotic shock, and is involved in T cell differentiation and apoptosis.

The term "mimetic" in connection with a compound refers to a compound in which chemical structures of the compound necessary for functional activity have been replaced with other chemical structures which mimic the conformation of the compound or peptides thereof.

The terms "sample" and "biological sample" refer to any sample suitable for the methods provided by the present invention. In one embodiment, the biological sample of the present invention is a tissue sample, e.g., a biopsy specimen such as samples from needle biopsy. In other embodiments, the biological sample of the present invention is a sample of bodily fluid, e.g., serum, plasma, urine, and ejaculate.

The term "effective amount" of a compound refers a non-toxic but sufficient amount of the compound that provides a desired effect. This amount may vary from subject to subject, depending on the species, age, and physical condition of the subject, the severity of the disease that is being treated, the particular compound used, its mode of administration, and the like. Therefore, it is difficult to generalize an exact "effective amount," yet, a suitable effective amount may be determined by one of ordinary skill in the art.

The term "pharmaceutically acceptable" refers to a compound, additive or composition that is not biologically or otherwise undesirable. For example, the additive or composition may be administered to a subject along with a compound of the invention without causing any undesirable biological effects or interacting in an undesirable manner with any of the other components of the pharmaceutical composition in which it is contained.

The term "pharmaceutically acceptable salts" includes hydrochloric salt, hydrobromic salt, hydroiodic salt, hydrofluoric salt, sulfuric salt, citric salt, maleic salt, acetic salt, lactic salt, nicotinic salt, succinic salt, oxalic salt, phosphoric salt, malonic salt, salicylic salt, phenylacetic salt, stearic salt, pyridine salt, ammonium salt, piperazine salt, diethylamine salt, nicotinamide salt, formic salt, urea salt, sodium salt, potassium salt, calcium salt, magnesium salt, zinc salt, lithium salt, cinnamic salt, methylamino salt, methanesulfonic salt, picric salt, tartaric salt, triethylamino salt, dimethylamino salt, tris(hydroxymethyl)aminomethane salt and the like. Additional pharmaceutically acceptable salts are known to those of skill in the art.

As used herein, the term "patient" refers to organisms to be treated by the methods of the present invention. Such organisms include, but are not limited to, humans. In the context of the invention, the term "subject" generally refers to an individual who will receive or who has received treatment for the treatment of a disease, disorder or pathology.

The term "cancer" as used herein, includes any malignant tumor including, but not limited to, carcinoma, sarcoma. Cancer arises from the uncontrolled and/or abnormal division of cells that then invade and destroy the surrounding tissues. As used herein, "proliferating" and "proliferation" refer to cells undergoing mitosis. As used herein, "metastasis" refers to the distant spread of a malignant tumor from its sight of origin. Cancer cells may metastasize through the bloodstream, through the lymphatic system, across body cavities, or any combination thereof.

The term "cancerous cell" as used herein, includes a cell afflicted by any one of the cancerous conditions provided herein. Thus, the methods of the present invention include treatment of benign overgrowth of melanocytes, glia, prostate hyperplasia, and polycystic kidney disease. The term "carcinoma" refers to a malignant new growth made up of epithelial cells tending to infiltrate surrounding tissues, and to give rise to metastases.

The term "ameliorating" or "treating" means that the clinical signs and/or the symptoms associated with the disease, such as cancer, are lessened as a result of the actions performed.

According to embodiments of the present invention, there are provided compounds having the general structure A or pharmaceutically acceptable salts thereof:

$$\text{Het-L-P} \qquad (A)$$

wherein Het is an aromatic moiety comprising a heterocyclic structure, P is a peptide moiety comprising a peptide or a polypeptide, and L is a linking moiety, wherein L links the aromatic moiety to the peptide moiety.

In some embodiments, the aromatic moiety Het comprises a derivative of indazole including the following moiety:

wherein R is an aromatic substituent, e.g., an unsubstituted or substituted phenylene group, and $R_1$ is hydrogen or a substitutent selected from a group consisting of a straight-chained alkyl, a branched alkyl, and a halogen, and wherein the moiety Het is connected to the linking moiety via the aromatic substitutent R.

In some embodiments of the invention, in compounds of the general structure A, the linking moiety L is a di-amide structure, i.e., the linking moiety L comprises two terminal amido groups connected by a hydrocarbon bridge and has the following structure,

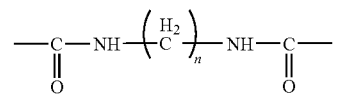

wherein the bridge can include between two and eight consecutively positioned methylene groups. In other embodiments, examples of a linking moiety L that can be used include the structures $-(CH_2)_n-$, $-O-(CH_2)_n-O-$, $-(CH_2)$-phenylene-, $-NHSO_2-(CH_2)_n-CONH-$, and $-CONH-(CH_2)_n-CONH-$, wherein n is an integer having the value between 2 and 8.

Compounds having the general structure A shown above include a peptide moiety P. When the compound is brought in contact with a kinase, the peptide moiety P can bind to the kinase docking site. Those having ordinary skill in the art can determine what particular peptides could be used in compound A. Typical non-limiting examples of some specific peptides that can be so used include $Xaa_{(0-8)}LNLGGXaa_{(0-8)}$ (SEQ ID NO:8), $Xaa_{(0-8)}LNLXaa_{(0-8)}$ (SEQ ID NO:9), an L optical isomer of any of RPTTLNLGG (SEQ ID NO:1), PTTLNLGG (SEQ ID NO:2), LNLGG (SEQ ID NO:3), RPTTLNL (SEQ ID NO:4), PTTLNL (SEQ ID NO:10), or LNL (which can be optionally N-myristoilated, if desired) or small molecule mimetics thereof, a D optical isomer of any of GGLNLTTPR (SEQ ID NO:11), GGLNLTTP (SEQ ID NO:12), GGLNL (SEQ ID NO:13), LNLTTPR (SEQ ID NO:14), LNLTTP (SEQ ID NO:15), or LNL (which can be optionally C-myristoilated, if desired), or small molecule mimetics thereof. The peptide moiety may contain one or more amino acid derivatives, analogs, mimetics, or non-natural amino acids.

Examples of peptide derivatives include peptides in which an amino acid side chain, the peptide backbone, or the amino- or carboxy-terminus has been derivatized. An example of an analog of a naturally occurring peptide is a peptide which includes one or more non-naturally-occurring amino acids.

Examples of some specific compounds that are within the purview of the present invention and are described by the general structure A include compounds I-VIII:

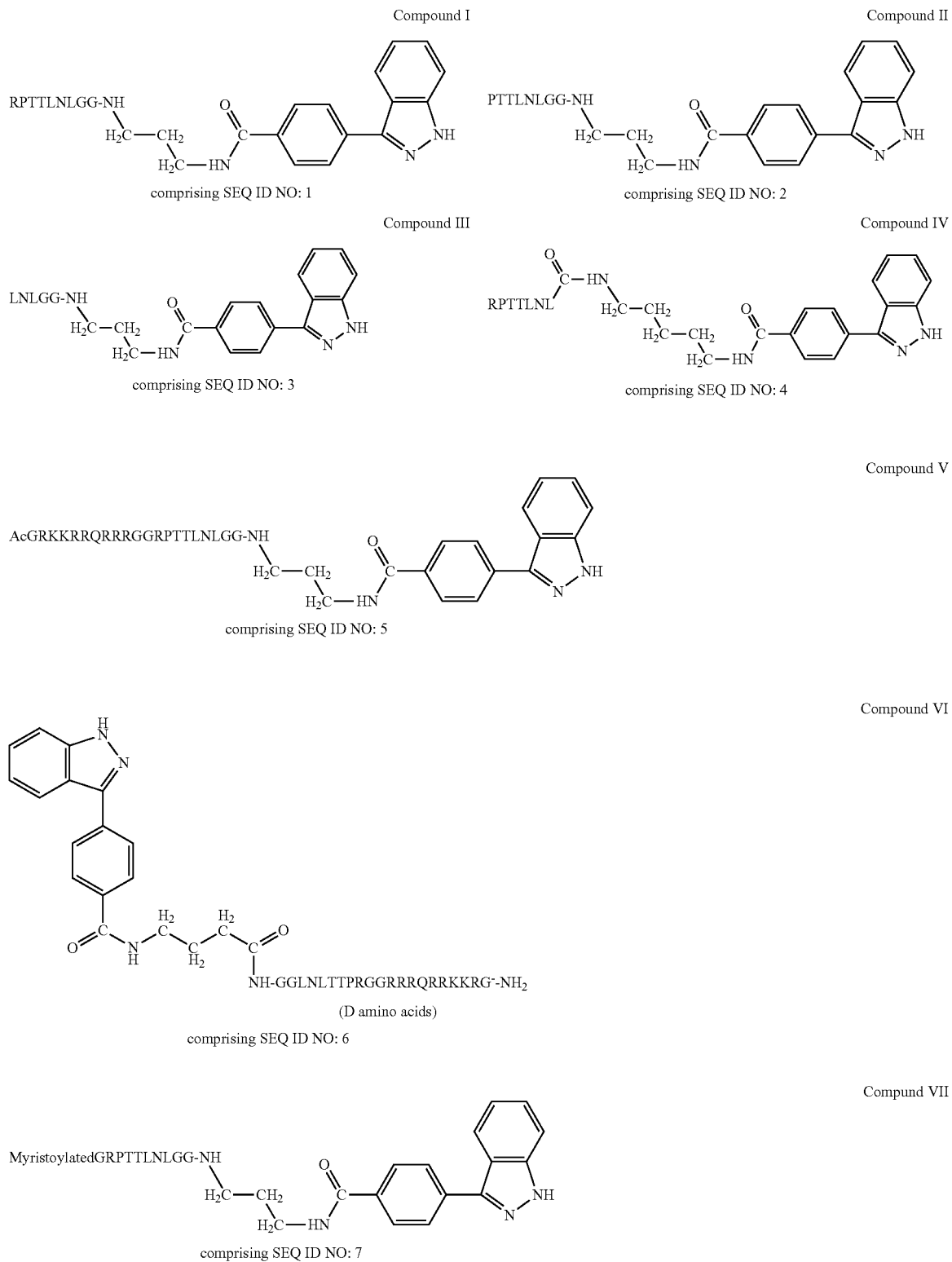

Compound VIII

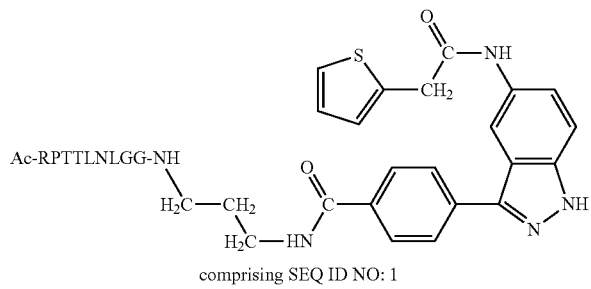

comprising SEQ ID NO: 1

As can be seen from the above formulae, each of the compounds I-VIII is an adduct which is a product of conjugation of a benzamide to the respective peptide, i.e., to the peptide RPTTLNLGG (SEQ ID NO:1), PTTLNLGG (SEQ ID NO:2), LNLGG (SEQ ID NO:3), or RPTTLNL (SEQ ID NO:4); for example, for compounds I-III, the benzamide is N-(aminopropyl)-4-(1-H-indazol-3-yl)benzamide.

In another aspect of the invention, the subject compounds can be used as part of a treatment regimen for cancer. In some cases, the treatment of cancer may include the treatment of solid tumors or the treatment of metastasis. Metastasis is a form of cancer wherein the transformed or malignant cells are traveling and spreading the cancer from one site to another. Such cancers include cancers of the skin, breast, brain, cervix, testes, etc. More particularly, cancers may include, but are not limited to the following organs or systems: cardiac, lung, gastrointestinal, genitourinary tract, liver, bone, nervous system, gynecological, hematologic, skin, and adrenal glands. More particularly, the methods herein can be used for treating gliomas (Schwannoma, glioblastoma, astrocytoma), neuroblastoma, pheochromocytoma, paraganlioma, meningioma, adrenalcortical carcinoma, kidney cancer, vascular cancer of various types, osteoblastic osteocarcinoma, prostate cancer, ovarian cancer, uterine leiomyomas, salivary gland cancer, choroid plexus carcinoma, mammary cancer, pancreatic cancer, colon cancer, and megakaryoblastic leukemia. Skin cancer includes malignant melanoma, basal cell carcinoma, squamous cell carcinoma, Karposi's sarcoma, moles dysplastic nevi, lipoma, angioma, dermatofibroma, keloids, and psoriasis. Thus, exemplary cancers that can be treated with the compounds of the invention include, but are not limited to, cancers of the brain, genitourinary tract, lymphatic system, stomach, larynx and lung.

In another aspect, the compounds are useful in the treatment of diseases where suppression, attenuation of the activity, and/or inhibiting kinases, for example, such kinases as JNK, p38, ERK, SRC, or JAK may be desirable. These include, but are not limited to, diabetes (both type I and type II), cerebral ischemia and stroke, neuropathic pain, neurological disorders and neurodegeneration, hepatic injury, treatment of viral infections, lung ischemia/reperfusion damage, acoustic trauma, macular degeneration, retinal vascularization, diabetic retinopathy, cancer, and inflammation. Moreover, the compounds described in the invention may be useful in clinical transplantation of pancreatic islet b-cells.

As such, the invention provides methods of treating cancer in a subject. Such methods include administering to an individual or a cell, a therapeutically effective amount of a compound of the invention. Generally the subject is human, although as will be appreciated by those in the art, the subject may be an animal. Thus other animals, including mammals such as rodents (including mice, rats, hamsters and guinea pigs), cats, dogs, rabbits, farm animals including cows, horses, goats, sheep, pigs, etc., and primates (including monkeys, chimpanzees, orangutans and gorillas) are included within the definition of subject. However, the method can also be practiced in other species, such as avian species (e.g., chickens).

In another aspect, the present invention provides a method of ameliorating or treating a tumor in a subject with the compounds of the invention. The signs or symptoms to be monitored will be characteristic of a particular cancer or melanoma and will be well known to the skilled clinician, as will the methods for monitoring the signs and conditions. For example, the skilled clinician will know that the size or rate of growth of a tumor can monitored using a diagnostic imaging method typically used for the particular tumor (e.g., using ultrasound or magnetic resonance image (MRI) to monitor a tumor).

Accordingly, the methods of the invention are useful for providing a means for practicing personalized medicine, wherein treatment is tailored to a subject based on the particular characteristics of the cancer cells in the subject. In one embodiment, the method can be practiced by contacting a sample of cells from the subject with at least one compound of the invention, and measuring the ability of the compound to displace the binding between JNK and the L-JIP peptide. In another embodiment, the method can be practiced by contacting a sample of cells from the subject with at least one compound of the invention, and measuring the ability of the compound to inhibit JNK-mediated phosphorylation of substrates. In yet another embodiment, the method can further include testing the compound against a related kinase, e.g., p38 to demonstrate selectivity and identify the compound as useful for treating the cancer.

The sample of cells examined according to the present method can be obtained from the subject to be treated, or can be cells of an established cancer cell line of the same type as that of the subject. In one aspect, the established cancer cell line can be one of a panel of such cell lines, wherein the panel can include different cell lines of the same type of cancer and/or different cell lines of different cancers. Such a panel of cell lines can be useful, for example, to practice the present method when only a small number of cancer cells can be obtained from the subject to be treated, thus providing a surrogate sample of the subject's cancer, and also can be useful to include as control samples in practicing the present methods.

Preferred cell types for use in the invention include, but are not limited to, mammalian cells, including animal (rodents, including mice, rats, hamsters and gerbils), primates, and human cells, particularly cancer cells of all types, including breast, skin, lung, cervix, testes, colorectal, leukemia, brain, etc.

Once disease is established and a treatment protocol is initiated, the methods of the invention may be repeated on a regular basis to evaluate whether displacement of the binding between JNK and the L-JIP peptide and/or inhibition of JNK-mediated phosphorylation in the subject begins to approximate that which is observed in a normal subject. The results obtained from successive assays may be used to show the efficacy of treatment over a period ranging from several days to months. Accordingly, the invention is also directed to methods for monitoring a therapeutic regimen for treating a subject having cancer. A comparison of the level of displacement of the binding between JNK and the L-JIP peptide and/or inhibition of JNK-mediated phosphorylation prior to and during therapy indicates the efficacy of the therapy. Therefore, one skilled in the art will be able to recognize and adjust the therapeutic approach as needed.

Accordingly, the compounds having the structure A, including the specific compounds I-VIII, or pharmaceutically acceptable salts thereof can be used for preparing pharmaceutical compositions, e.g., by combining these compounds and pharmaceutically acceptable carriers. The pharmaceutical compositions can then be used in pharmacologically effective doses for the treatment of various disorders, diseases, and pathologies, such as cancer, diabetes (including diabetic retinopathy), neurological disorders, diseases in which angiogenesis is implicated (e.g., ocular diseases), and retinal vascularization.

If the pharmaceutical compositions are used for the treatment of cancer, the kinds of cancer that can be so treated include, for example, cancers of the brain, genitourinary tract, lymphatic system (e.g., histiocytic lymphoma), stomach, larynx, lung (e.g., lung adenocarcinoma or small cell lung cancers), pancreatic cancer, glioblastomas, breast cancer (e.g., breast carcinoma), colorectal cancer, and prostate cancer.

Various synthetic schemes can be designed for manufacturing the products having the structure A, including the specific compounds I-VIII. To exemplify, but not limit, the present invention, in one embodiment, the reaction scheme (A) shown below in the "Examples" portion of the application can be employed for making compound I. If desired, other synthetic processes can be designed by those having ordinary skill in the art.

Pharmaceutically acceptable salts of the compounds of the present invention may be obtained using standard procedures well known in the art, for example by reacting a sufficiently basic compound such as an amine with a suitable acid affording a physiologically acceptable anion. Alkali metal (for example, sodium, potassium or lithium) or alkaline earth metal (for example calcium) salts of carboxylic acids can also be made.

The above-described compounds A, including the subgenera I-VIII can be formulated as pharmaceutical compositions and administered to a mammalian host, such as a human patient in a variety of forms adapted to the chosen route of administration, e.g., orally or parenterally, by intravenous, intraperitoneal, intramuscular, topical or subcutaneous routes.

Thus, the present compounds may be systemically administered, e.g., orally, in combination with a pharmaceutically acceptable vehicle such as an inert diluent or an assimilable edible carrier. They may be enclosed in hard or soft shell gelatin capsules, may be compressed into tablets, or may be incorporated directly with the food of the patient's diet. For oral therapeutic administration, the active compound may be combined with one or more excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 60% of the weight of a given unit dosage form. The amount of active compound in such therapeutically useful compositions is such that an effective dosage level will be obtained.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound may be incorporated into sustained-release preparations and devices.

The active compound may also be administered intravenously or intraperitoneally by infusion or injection. Solutions of the active compound or its salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

The pharmaceutical dosage forms suitable for injection or infusion can include sterile aqueous solutions or dispersions or sterile powders comprising the active ingredient which are adapted for the extemporaneous preparation of sterile injectable or infusible solutions or dispersions, optionally encapsulated in liposomes. In all cases, the ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions are prepared by incorporating the active compound in the required amount in the appropriate solvent with various of the other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

For topical administration, the present compounds may be applied in pure form, i.e., when they are liquids. However, it will generally be desirable to administer them to the skin as compositions or formulations, in combination with a dermatologically acceptable carrier, which may be a solid or a liquid.

Useful solid carriers include finely divided solids such as talc, clay, microcrystalline cellulose, silica, alumina and the like. Useful liquid carriers include water, alcohols or glycols or water-alcohol/glycol blends, in which the present compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

Useful dosages of the compounds A, including the species I-VIII can be determined by comparing their in vitro activity, and in vivo activity in animal models. Methods for the extrapolation of effective dosages in mice, and other animals, to humans are known to those having ordinary skill in the art who can, for example, be guided by the procedures described in U.S. Pat. No. 4,938,949.

Generally, the concentration of the compounds A, including the species I-VIII in a liquid composition, such as a lotion, can be between about 0.1 and 25 mass %, such as between about 0.5 and 10 mass %. The concentration in a semi-solid or solid composition such as a gel or a powder can be between about 0.1 and 25 mass %, such as between about 0.5 and 2.5 mass %.

The amount of the compounds A, including the species I-VIII, or an active salt or derivative thereof, required for use in treatment will vary not only with the particular salt selected but also with the route of administration, the nature of the condition being treated and the age and condition of the patient and will be ultimately at the discretion of the attendant physician or clinician.

In general, however, a suitable dose can be in the range of between about 0.5 and 100 mg/kg, e.g., between about 10 and 75 mg/kg of body weight per day, such as between about 15 and 60 mg/kg/day. The compounds A, including the species I-VIII can be conveniently administered in unit dosage form; for example, containing 5 to 1000 mg, such as 10 to 750 mg, for example, 50 to 500 mg of active ingredient per unit dosage form. The desired dose may conveniently be presented in a single dose or as divided doses administered at appropriate intervals, for example, as two, three, four or more sub-doses per day. The sub-dose itself may be further divided, e.g., into a number of discrete loosely spaced administrations.

Optionally, the compositions of the present invention can be administered to a patient in need thereof in combination with other therapeutically beneficial agent(s). Such additional therapeutically beneficial agent(s) can include an estrogen receptor modulator, an androgen receptor modulator, a retinoid receptor modulator, a cytotoxic agent, an antiproliferative agent, a prenyl-protein transferase inhibitor, an HMG-CoA reductase inhibitor, an HIV protease inhibitor, a reverse transcriptase inhibitor, an angiogenesis inhibitor, or a PPAR-gamma agonist.

If an additional angiogenesis inhibitor is used in combination with the compositions of the present invention, examples of specific angiogenesis inhibitors that can be so used include a tyrosine kinase inhibitor, an inhibitor of epidermal-derived growth factor, an inhibitor of fibroblast-derived growth factor, an inhibitor of platelet derived growth factor, an MMP inhibitor, an integrin blocker, interferon-alpha, interleukin-12, pentosan polysulfate, a cyclooxygenase inhibitor, carboxyamidotriazole, combretastatin A-4, squalamine, 6-O-(chloroacetyl-carbonyl)-fumagillol, thalidomide, angiostatin, troponin-1, or an antibody to VEGF.

In addition, optionally, the compositions of the present invention can be administered to a patient in need thereof in combination with a steroidal anti-inflammatory compound or with an anti-hypertensive compound.

EXAMPLES

The following examples are intended to further illustrate but not limit the scope of the invention.

Example 1

Synthesis of Compound I

Compound I comprising SEQ ID NO:1 shown above was synthesized according to the reaction scheme (A).

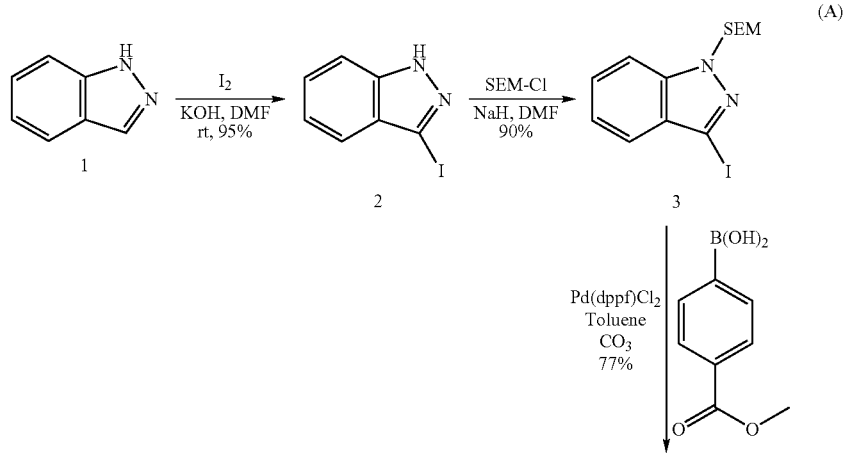

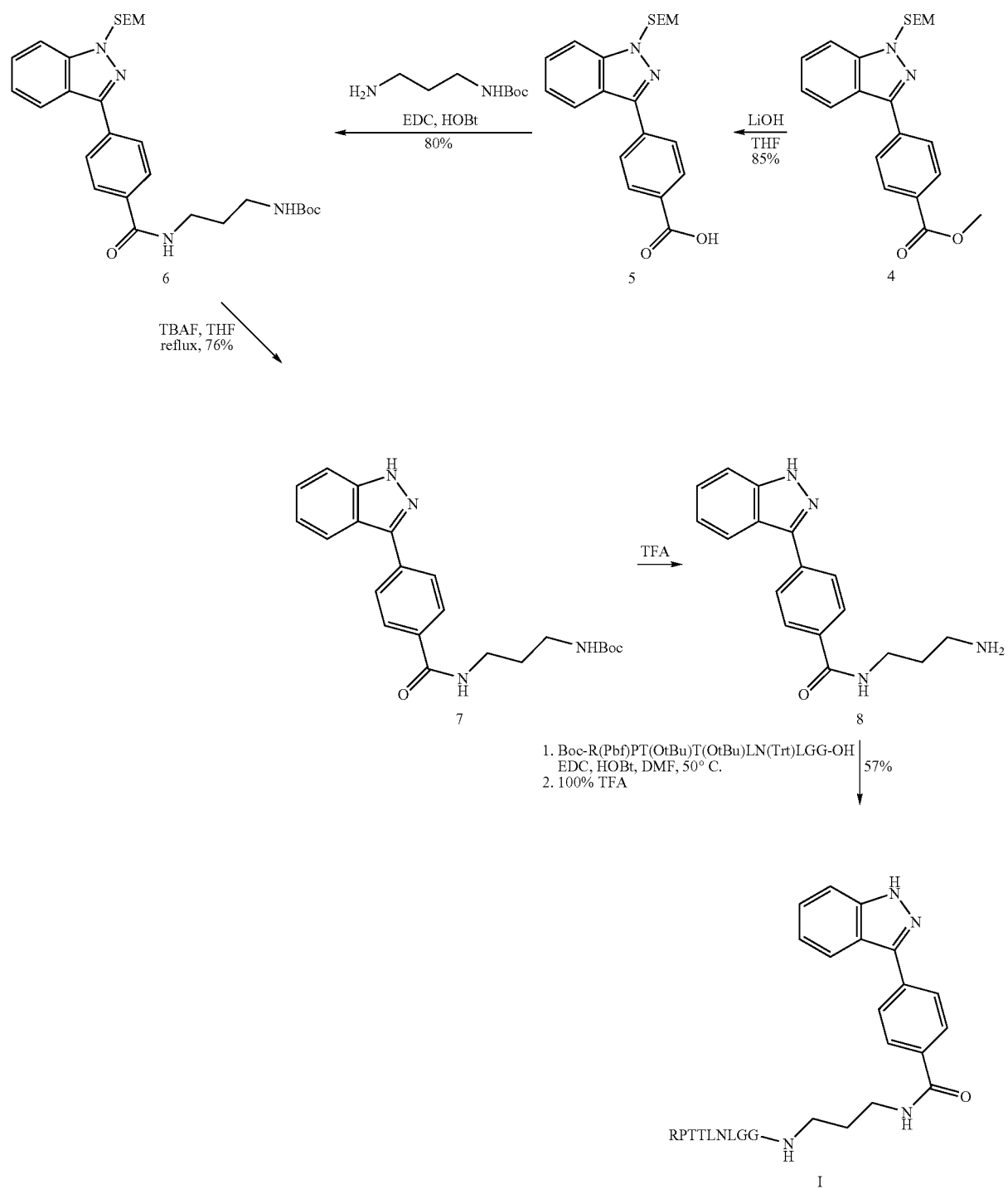

Example 2

Properties of Compounds of the Invention

Compounds of the present invention were tested using Delfia Assay and Kinase Assay and the data for IC$_{50}$ were obtained. The results are shown in Tables 1 (both assays) and 2 (Kinase Assay only). The data for various peptides not bonded to any compounds of the present invention is provided in Table 1 for comparison purposes.

TABLE 1

Comparative Results on Inhibition Using Compounds

| Compound | IC$_{50}$, µM | | |
| --- | --- | --- | --- |
| | Delfia Assay (Displacement of L-JIP1 peptide from JNK) | Kinase Activity Assay (JNK) | Kinase Activity Assay (p38α) |
| 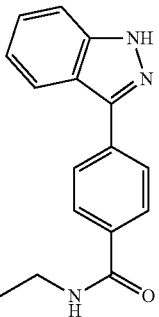<br>Compound I comprising SEQ ID NO: 1 | 0.002 | 0.0007 | 0.19 |
| 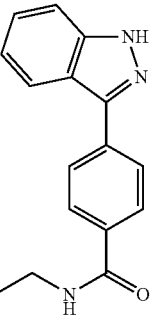<br>Compound II comprising SEQ ID NO: 2 | 0.08 | 0.15 | ND |
| 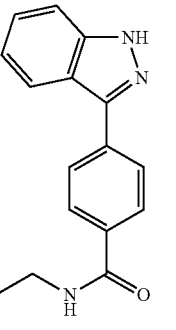<br>Compound III comprising SEQ ID NO: 3 | 0.6 | 0.3 | ND |

TABLE 1-continued

Comparative Results on Inhibition Using Compounds

| Compound | IC$_{50}$, μM | | |
|---|---|---|---|
| | Delfia Assay (Displacement of L-JIP1 peptide from JNK) | Kinase Activity Assay (JNK) | Kinase Activity Assay (p38α) |
| Compound V comprising SEQ ID NO: 5 | 0.026 | 0.002 | ND |
| Compound VI comprising SEQ ID NO: 6 (D amino acids) | 3.2 | 0.18 | 0% at 50 μM |
| Compound VII comprising SEQ ID NO: 7 | 0.047 | 0.007 | 25% at 50 μM |
| Compound VIII comprising SEQ ID NO: 1 | 0.001 | 0.0003 | 3% at 50 μM |

TABLE 1-continued

Comparative Results on Inhibition Using Compounds

| Compound | IC$_{50}$, μM | | |
|---|---|---|---|
| | Delfia Assay (Displacement of L-JIP1 peptide from JNK) | Kinase Activity Assay (JNK) | Kinase Activity Assay (p38α) |
| 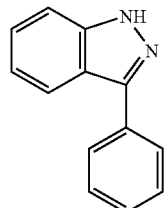<br>Product 8 on Scheme (A) | ND*⁾ | 14 | ND |
| 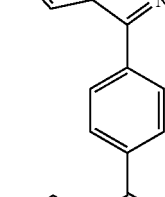<br>Product 7 on a Scheme (A) | ND*⁾ | 3.5 | ND |
| Ac-RPKRPTTLNLF (L-JIP Peptide) (SEQ ID NO: 16) | 2.9 | 0.423 | 6% at 50 μM |
| AcGRKKRRQRRRGGRPTTLNLGG (HIV TAT L-JIP peptide) (SEQ ID NO: 5) | ND | 90% inhibition at 50 μM | 6% at 50 μM |
| GGLNLTTPRGGRRRQRRKKRG-NH$_2$ (D-aminoacids) (HIV TAT D-JIP peptide) (SEQ ID NO: 6) | ND | 11% inhibition at 50 μM | 0% at 50 μM |
| Ac-RPTTTLNLGG-OH (SEQ ID NO: 1) | 18 | 25% at 50 μM | |
| Ac-PTTLNLGG-OH (SEQ ID NO: 2) | ND*⁾ | ND*⁾ | ND |
| Ac-LNLGG-OH (SEQ ID NO: 3) | ND*⁾ | ND*⁾ | ND |
| Ac-LNL-OH | ND*⁾ | ND*⁾ | ND |

*⁾ND: In the Delfia Assay, no displacement up to 100 μM; in the Kinase Assay, no activity at 25 μM.

TABLE 2

Comparative Results on Inhibition Using Compounds of the Present Invention

[Structure: 1H-indazole with R2 at 6-position, R3 at 5-position, and 3-(4-R1-phenyl) substituent] ⇓ Linker & Peptide

| Compound R1 | R2 | R3 | IC50 (μM) |
| --- | --- | --- | --- |
| H | H | NO₂ | 41% at 25 μM |
| CH₂C(O)OH | H | H | 5.4 |
| CH₂C(O)OMe | H | H | 9.7 |
| CH₂C(O)NH(CH₂)₃NH₂ | H | H | 14 |
| CH₂C(O)NH(CH₂)₃NH₂ | H | CH₂C(O)NHCH₂-(2-thienyl) | 1.9 |
| CH₂C(O)NH(CH₂)₃C(O)OH | H | H | 1.4 |
| CH₂C(O)NH(CH₂)₃C(O)OMe | H | H | 0.9 |
| CH₂C(O)NH(CH₂)₃NHBoc | H | H | 3.5 |
| CH₂C(O)NH(CH₂)₃NHBoc | H | CH₂C(O)NHCH₂-(2-thienyl) | 1.2 |

TABLE 2-continued
Comparative Results on Inhibition Using Compounds of the Present Invention
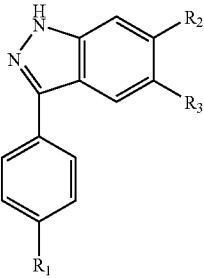
| Compound | | | IC50 |
|---|---|---|---|
| R1 | R2 | R3 | (μM) |
| 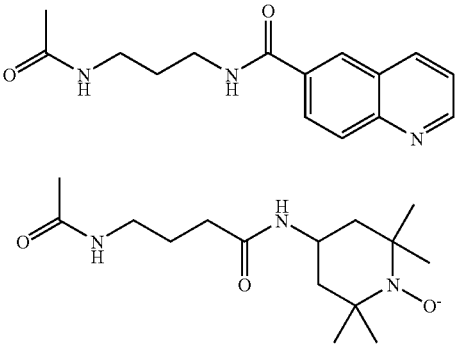 | H | H | 5.7 |
| 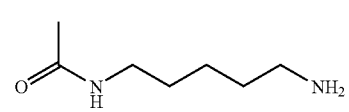 | H | H | 1.6 |
| 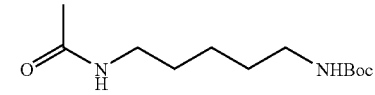 | H | H | 6.3 |
| 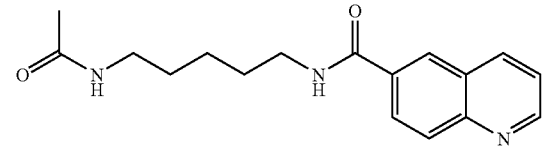 | H | H | 2.3 |
| 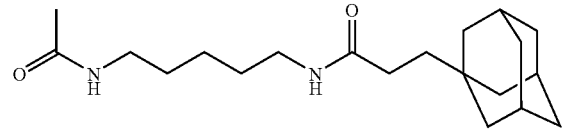 | H | H | 4.8 |
| 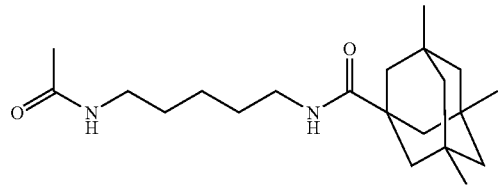 | H | H | 2.2 |
|  | H | H | 4.7 |

TABLE 2-continued

Comparative Results on Inhibition Using Compounds of the Present Invention

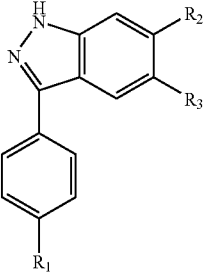

| Compound | | | IC50 |
|---|---|---|---|
| R1 | R2 | R3 | (μM) |
| 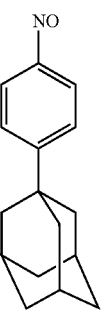 | H | H | 5.0 |
| 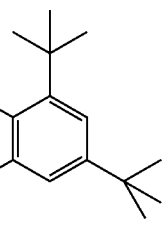 | H | H | 1.3 |
| 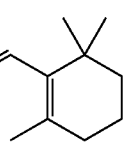 | H | H | 1.0 |
| 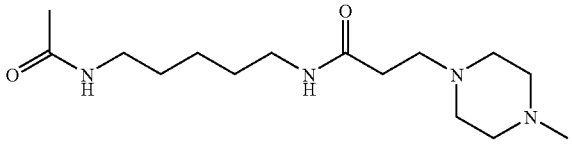 | H | H | 0.75 |
| | H | H | 4.5 |

Figure 1B:
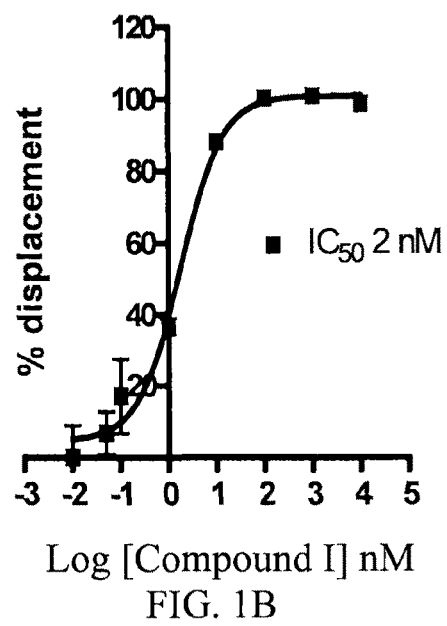
FIG. 1B illustrates kinase inhibition by a compound of the present invention.
Figure 1C:
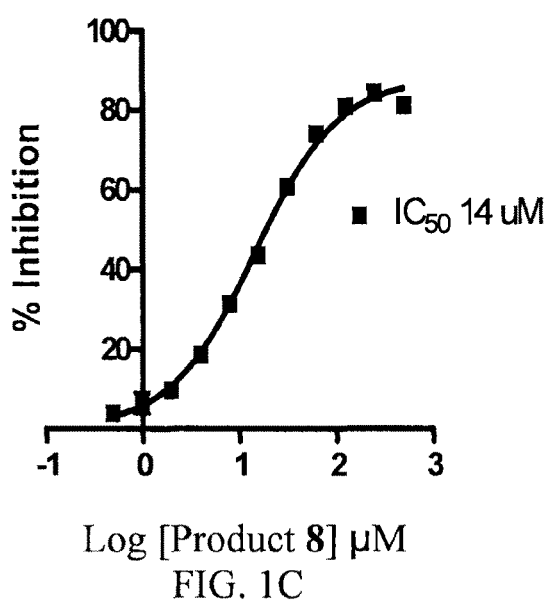
FIG. 1C illustrates kinase inhibition by a compound that is different from compounds of the present invention, which illustration is provided for the purposes of comparison.
Figure 1D:
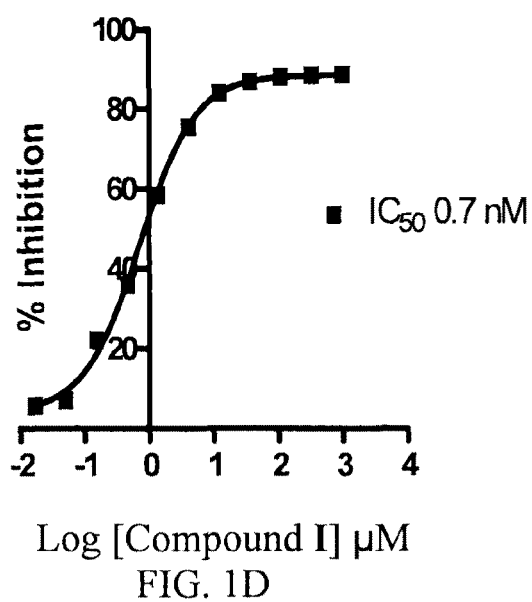
FIG. 1D illustrates kinase inhibition by a compound of the present invention.

FIGS. 1A-1D, 2A-2D, 3A, and 3B further exemplify embodiments of the present invention. FIGS. 1A and 1B illustrate kinase inhibition obtained in Delfia Assay for the peptide Ac-RPTTLNLGG-OH (SEQ ID NO:1) (FIG. 1A) and for compound I of the present invention (FIG. 1B). FIGS. 1C and 1D illustrate kinase inhibition obtained in Delfia Assay for the product 8 (FIG. 1C) and for compound I of the present invention (FIG. 1D). As can be seen, compound I is substantially more active as an inhibitor in both comparisons.

Figure 2A:
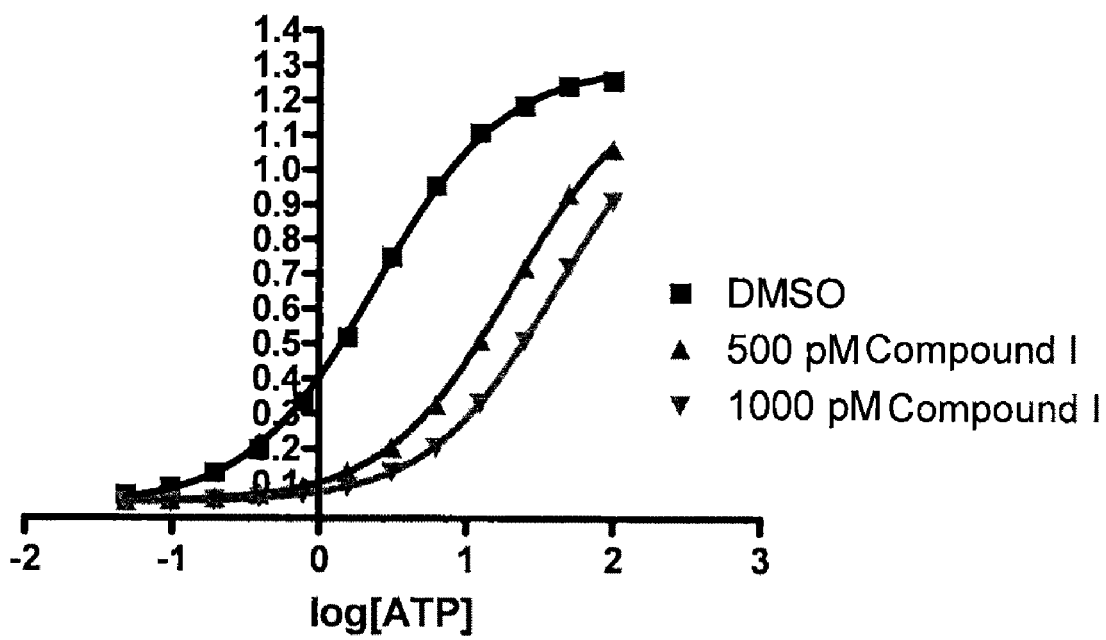
FIG. 2A provides the data on the ATP competition analysis for a compound of the present invention.
Figure 2B:
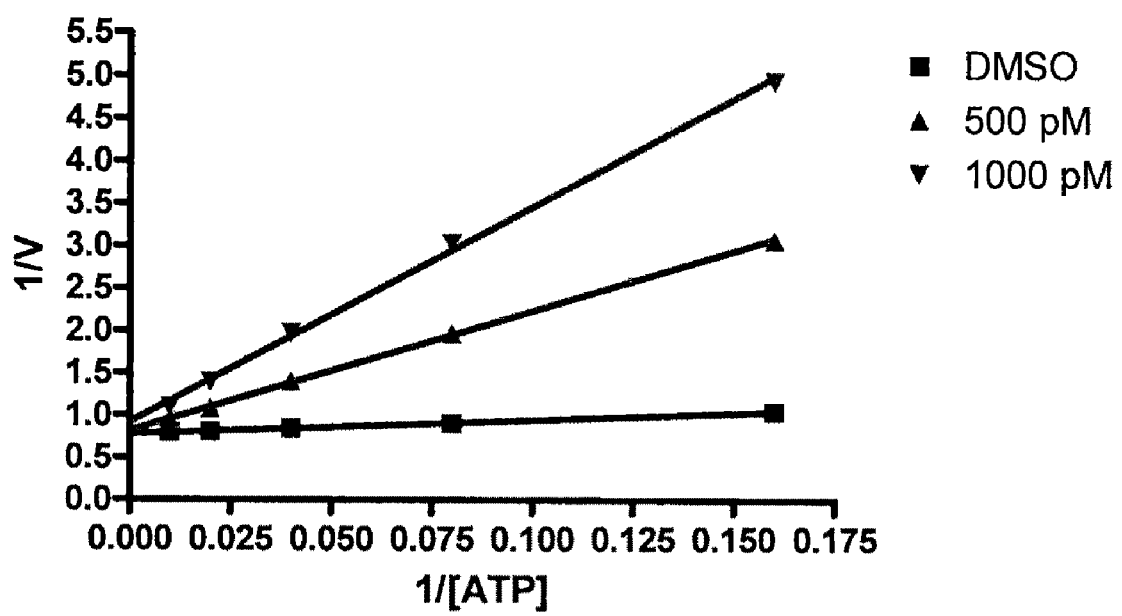
FIG. 2B provides further data on the ATP competition analysis for a compound of the present invention.
Figure 2C:
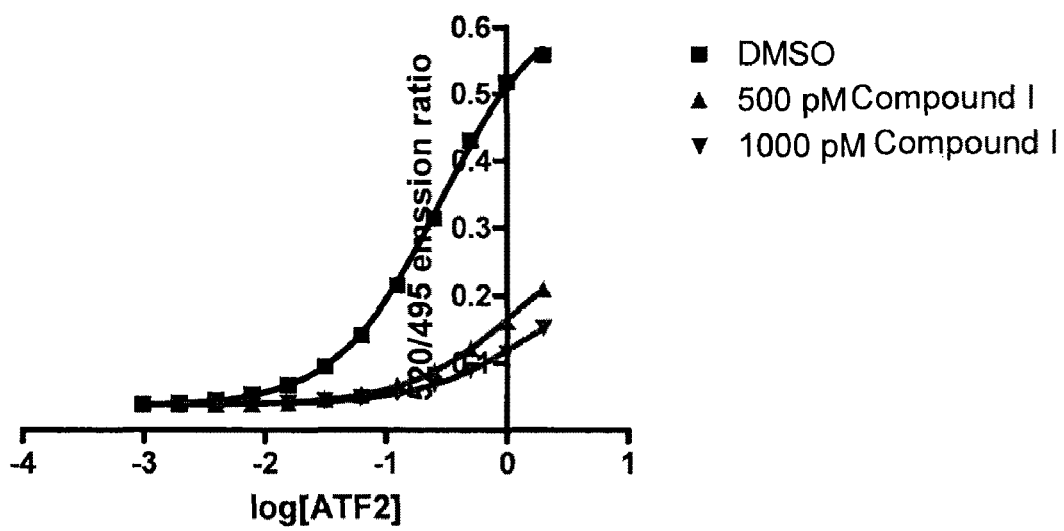
FIG. 2C provides the data on the ATF2 competition analysis for a compound of the present invention.
Figure 2D:
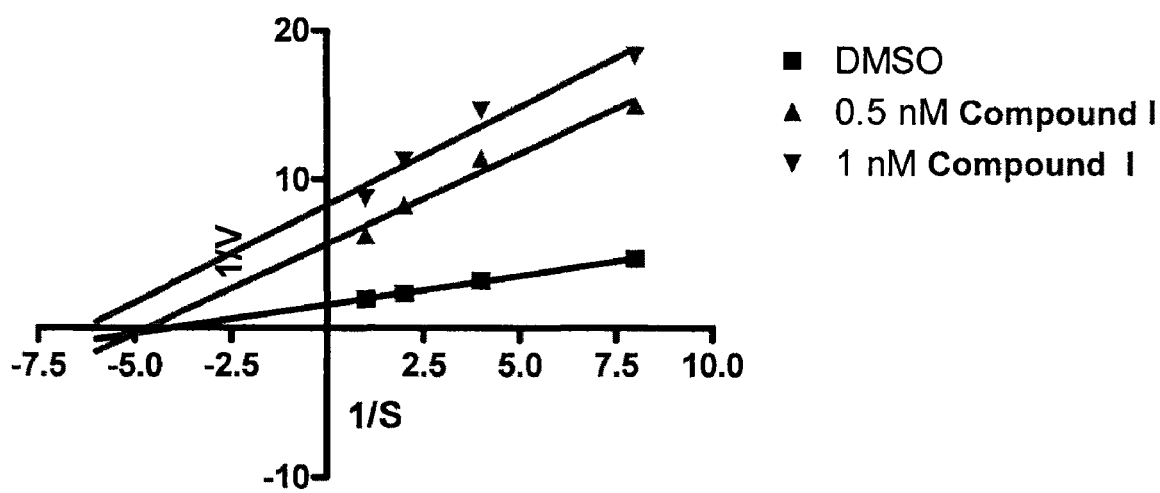
FIG. 2D provides further data on the ATF2 competition analysis for a compound of the present invention FIG. 3A provides the data on selectivity of a compound of the present invention relative to p38.
Figure 3A:
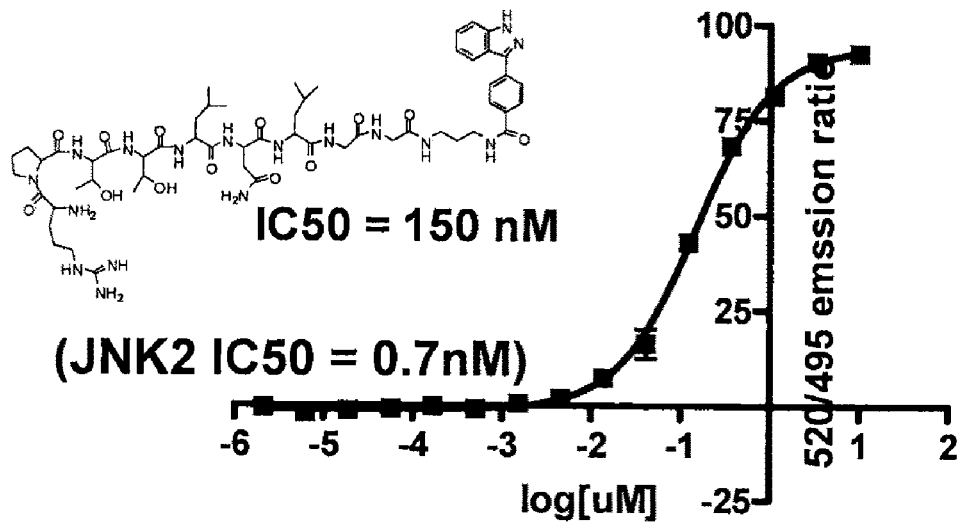
FIG. 3B provides the data on selectivity of another compound of the present invention relative to p38.
Figure 3B:
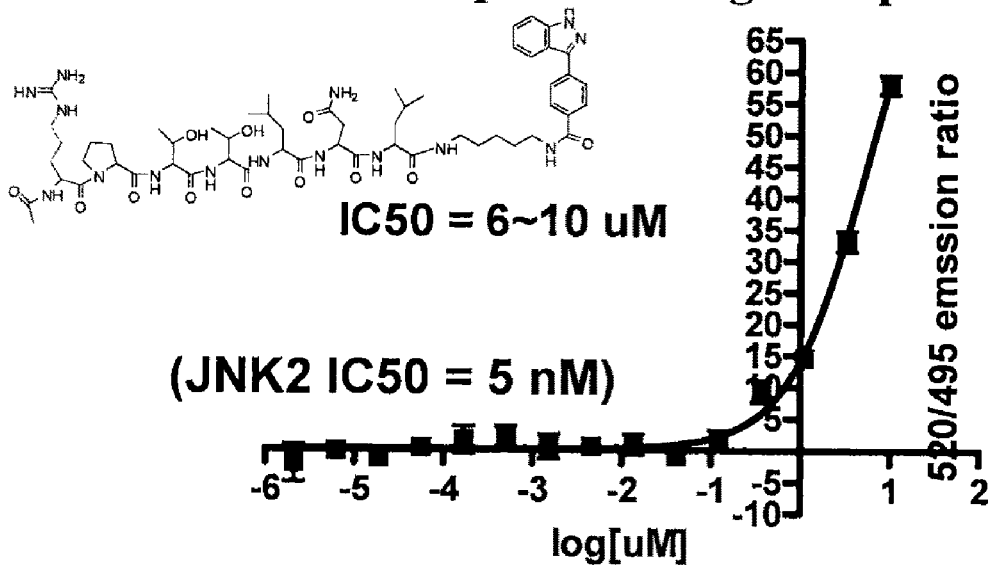

FIGS. 2A and 2B provide the data on the ATP competition analysis for Compound I, and FIGS. 2C and 2D the data on the ATF2 competition analysis for Compound I. These data demonstrate that Compound I is competitive, at least to some extent, in both sets of experiments. FIGS. 3A and 3B further demonstrate that both Compound I (FIG. 3A) and Compound IV (FIG. 3B) possess good selectivity relative to p38a.

Although the invention has been described with reference to the above examples, it will be understood that modifications and variations are encompassed within the spirit and scope of the invention. Accordingly, the invention is limited only by the following claims.

What is claimed is:

1. A compound having the general structure A or a pharmaceutically acceptable salt thereof:

Het-L-P    (A)

wherein:

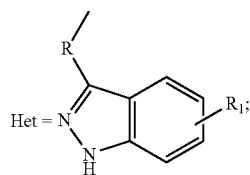

R is phenylene;
   $R_1$ is hydrogen, straight-chained alkyl, branched alkyl, halogen, nitro or $NHC(O)CH_2C_4H_3S$;
   P is a peptide consisting of the sequence selected from the group consisting of RPTTLNLGG (SEQ ID NO:1), PTTLNLGG (SEQ ID NO:2), LNLGG (SEQ ID NO:3), RPTTLNL (SEQ ID NO:4), GRKKRRGRRRGGRPT-TLNLGG (SEQ ID NO:5), GGLNLTTPRGGRRRQR-RKKRG (SEQ ID NO:6, (D amino acids)), GRPTTLN-LGG (SEQ ID NO:7); $Xaa_{(0-8)}LNLGGXaa_{(0-8)}$ (SEQ ID NO:8), PTTLNL (SEQ ID NO:10), GGLNLTTPR (SEQ ID NO:11), GGLNLTTP (SEQ ID NO:12), GGLNL (SEQ ID NO:13), LNLTTPR (SEQ ID NO:14), LNLTTP (SEQ ID NO: 15), LNL, N-myristoilated RPT-TLNLGG (SEQ ID NO:1), N-myristoilated PTTLN-LGG (SEQ ID NO:2), N-myristoilated LNLGG (SEQ ID NO:3), N-myristoilated RPTTLNL (SEQ ID NO:4), N-myristoilated PTTLNL (SEQ ID NO:10), N-myristoilated LNL, C-myristoilated GGLNLTTPR (SEQ ID NO:11), C-myristoilated GGLNLTTP (SEQ ID NO:12), C-myristoilated GGLNL (SEQ ID NO:13), C-myristoilated LNLTTPR (SEQ ID NO:14), C-myristoilated LNLTTP (SEQ ID NO:15) and C-myristoilated LNL, and L is a linking moiety selected from the group consisting of: (a) structure II:

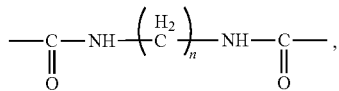

(b) $-(CH_2)_n-$, (c) $-O-(CH_2)_n-O-$, (d) $-(CH_2)$-phenylene-, and (e) $-NHSO_2-(CH_2)_n-CONH-$, wherein n is an integer having a value between 2 and 8, and wherein Het is connected to the linking moiety L via the phenylene substituent R, and wherein the linking moiety L links the phenylene substituent R to the peptide P.

2. The compound of claim 1, wherein the peptide moiety binds to a JNK kinase docking site.

3. The compound of claim 2, wherein the peptide consists of $Xaa_{(0-8)}LNLGGXaa_{(0-8)}$ (SEQ ID NO:8).

4. The compound of claim 2, wherein the peptide is an L optical isomer of a peptide consisting of the sequence selected from the group consisting of RPTTLNLGG (SEQ ID NO:1), PTTLNLGG (SEQ ID NO:2), LNLGG (SEQ ID NO:3), RPTTLNL (SEQ ID NO:4), PTTLNL (SEQ ID NO:10), LNL, and N-myristoilated sequences thereof.

5. The compound of claim 4, wherein the peptide is N-myristoilated.

6. The compound of claim 2, wherein the peptide is a D optical isomer of a any peptide consisting of the sequence selected from the group consisting of GGLNLTTPR (SEQ ID NO:11), GGLNLTTP (SEQ ID NO:12), GGLNL (SEQ ID NO:13), LNLTTPR (SEQ ID NO:14), LNLTTP (SEQ ID NO:15), and LNL, and C— myristoilated sequences thereof.

7. The compound of claim 6, wherein the peptide is C-myristoilated.

8. The compound of claim 1, wherein the linking moiety is structure II.

9. A compound selected from compounds I-VIII, wherein compounds I-VII comprise SEQ ID NO'S 1 to 7 and compound VIII comprises SEQ ID NO:1:

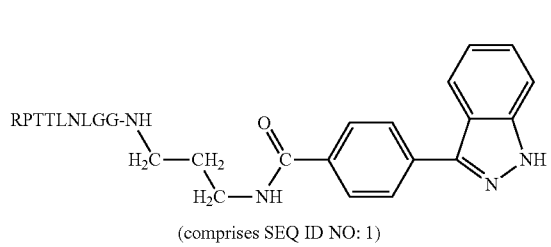

(comprises SEQ ID NO: 1)

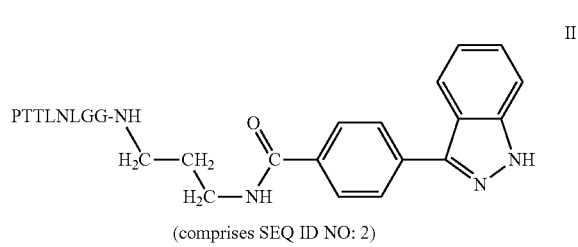

(comprises SEQ ID NO: 2)

-continued

III
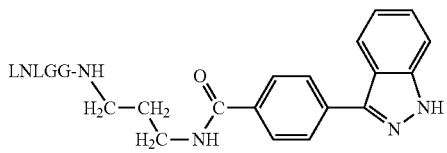
(comprises SEQ ID NO: 3)

IV
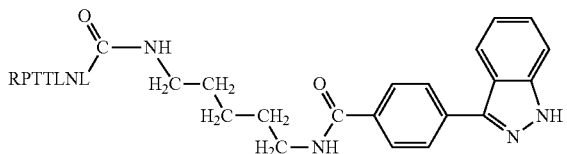
(comprises SEQ ID NO: 4)

V
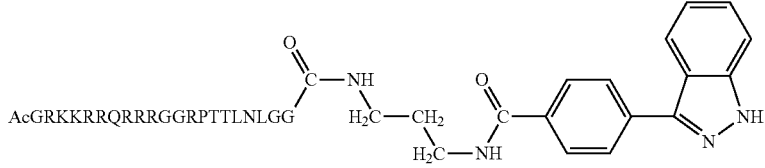
(comprises SEQ ID NO: 5)

VI
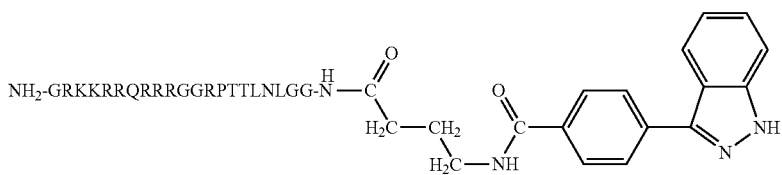
(comprises SEQ ID NO: 6 (D amino acids))

VII
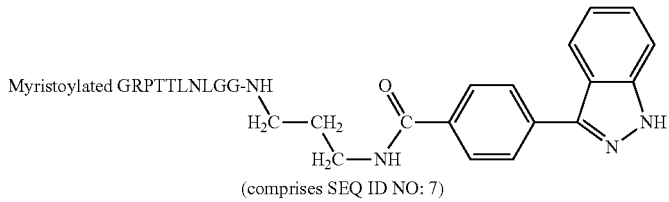
(comprises SEQ ID NO: 7)

VIII
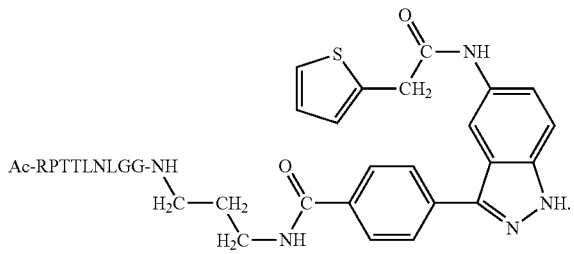
(comprises SEQ ID NO: 1)

10. A pharmaceutical composition comprising a compound of claim 1 or claim 9, and a pharmaceutically acceptable carrier thereof.

11. The composition of claim 9, further comprising an additional compound selected from:
   (1) an estrogen receptor modulator,
   (2) an androgen receptor modulator,
   (3) retinoid receptor modulator,
   (4) a cytotoxic agent,
   (5) an antiproliferative agent,
   (6) a prenyl-protein transferase inhibitor,
   (7) an HMG-CoA reductase inhibitor,
   (8) an HIV protease inhibitor,
   (9) a reverse transcriptase inhibitor,
   (10) an angiogenesis inhibitor, and
   (11) a PPAR-gamma agonist.

12. The composition of claim 11, wherein the additional compound is an angiogenesis inhibitor selected from a tyrosine kinase inhibitor, an inhibitor of epidermal-derived growth factor, an inhibitor of fibroblast-derived growth factor, an inhibitor of platelet derived growth factor, an MMP inhibitor, an integrin blocker, interferon-.alpha., interleukin-12, pentosan polysulfate, a cyclooxygenase inhibitor, carboxyamidotriazole, combretastatin A-4, squalamine, 6-O-(chloroacetyl-carbonyl)-fumagillol, thalidomide, angiostatin, troponin-1, and an antibody to VEGF.

13. The composition of claim 11, wherein the additional compound is an estrogen receptor modulator selected from tamoxifen and raloxifene.

14. The composition of claim 11, further comprising a steroidal anti-inflammatory compound.

15. The composition of claim 11, further comprising an anti-hypertensive compound.

16. A method of treating retinal vascularization, comprising administering to a subject a therapeutically effective amount of a composition of claim 10.

17. A method of treating diabetic retinopathy, comprising administering to a subject a therapeutically effective amount of a composition of claim 10.

18. A kit comprising a packaging material and the pharmaceutical composition of claim 10 contained within the packaging material, wherein the packaging material comprises a label which indicates that the composition can be used for treating a disorder, disease, or pathology in a subject in need thereof.

* * * * *